US011712219B2

(12) United States Patent
Abe

(10) Patent No.: US 11,712,219 B2
(45) Date of Patent: Aug. 1, 2023

(54) ULTRASONIC WAVE DIAGNOSTIC APPARATUS, MEDICAL INFORMATION PROCESSING APPARATUS, AND COMPUTER PROGRAM PRODUCT

(71) Applicant: CANON MEDICAL SYSTEMS CORPORATION, Otawara (JP)

(72) Inventor: Yasuhiko Abe, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 0 days.

(21) Appl. No.: 16/713,237

(22) Filed: Dec. 13, 2019

(65) Prior Publication Data
US 2020/0187897 A1 Jun. 18, 2020

(30) Foreign Application Priority Data
Dec. 14, 2018 (JP) .................................. 2018-234204

(51) Int. Cl.
*A61B 8/08* (2006.01)
*A61B 8/00* (2006.01)
*A61B 5/318* (2021.01)
(52) U.S. Cl.
CPC .......... *A61B 8/0883* (2013.01); *A61B 8/4416* (2013.01); *A61B 8/461* (2013.01); *A61B 8/5223* (2013.01); *A61B 5/318* (2021.01)
(58) Field of Classification Search
CPC ... A61B 8/0883; A61B 8/4416; A61B 8/5223; A61B 8/461; A61B 5/318; A61B 8/065;
(Continued)

(56) References Cited

U.S. PATENT DOCUMENTS

2008/0085043 A1* 4/2008 Watanabe ............... G06T 7/149
382/131
2014/0100461 A1* 4/2014 Abe ..................... A61B 8/5223
600/443
(Continued)

FOREIGN PATENT DOCUMENTS

JP 2002-140690 A 5/2002
JP 2015-114172 A 6/2015
(Continued)

OTHER PUBLICATIONS

Heart Valve, Wikipedia, https://web.archive.org/web/20160611123147/https://en.wikipedia.org/wiki/Heart_valve, wayback machine captured on Jun. 11, 2016.*
(Continued)

*Primary Examiner* — Bo Joseph Peng
(74) *Attorney, Agent, or Firm* — Oblon, McClelland, Maier & Neustadt, L.L.P.

(57) ABSTRACT

An ultrasonic wave diagnostic apparatus according to an embodiment includes processing circuitry. The processing circuitry acquires a plurality of pieces of volume data obtained through image capturing of a region including the cardiac ventricle of a subject for a predetermined duration. The processing circuitry estimates motion of tissue of the cardiac ventricle by using the pieces of volume data. The processing circuitry calculates, based on a result of the estimation, cardiac ventricle information indicating at least one of wall motion information and volume information related to the cardiac ventricle. The processing circuitry calculates, based on a result of the estimation, annulus information related to the size or shape of an annulus position of a valve related to inflow or outflow of blood current at the cardiac ventricle. The processing circuitry
(Continued)

outputs the cardiac ventricle information and the annulus information.

17 Claims, 9 Drawing Sheets

(58) Field of Classification Search
CPC ....... A61B 8/463; A61B 8/466; A61B 8/0891; A61B 8/483; A61B 8/485; A61B 8/5207; A61B 8/5292; A61B 8/543; A61B 8/469; A61B 8/06
See application file for complete search history.

(56) References Cited

U.S. PATENT DOCUMENTS

| | | | | |
|---|---|---|---|---|
| 2015/0018684 A1* | 1/2015 | Abe | ............. | A61B 8/14 600/443 |
| 2016/0140711 A1* | 5/2016 | Abe | ............. | A61B 8/483 382/128 |
| 2018/0279997 A1 | 10/2018 | Abe | | |

FOREIGN PATENT DOCUMENTS

| | | | |
|---|---|---|---|
| JP | 2016-093302 | A | 5/2016 |
| JP | 2017-074320 | A | 4/2017 |
| JP | 2018-068639 | A | 5/2018 |
| JP | 2018-171317 | A | 11/2018 |
| WO | WO 2006/068271 | A1 | 6/2006 |

OTHER PUBLICATIONS

"TOMTEC: 4D RV-Function", TOMTEC Imaging Systems GmbH, https://www.tomtec.de/products/application-finder/4d-rv-function / 7 pages.
U.S. Appl. No. 15/940,004, filed Mar. 29, 2018, 2018/0279997 A1, Abe, Y.
Office Action dated Jul. 28, 2022, in Chinese Patent Application No. 201911281819.9.
Office Action dated Sep. 27, 2022, in Japanese Patent Application No. 2018-234204.
Office Action dated Mar. 11, 2023, in Chinese Patent Application No. 201911281819.9 filed Dec. 13, 2019, 11 pages.

* cited by examiner

ULTRASONIC WAVE DIAGNOSTIC APPARATUS, MEDICAL INFORMATION PROCESSING APPARATUS, AND COMPUTER PROGRAM PRODUCT

CROSS-REFERENCE TO RELATED APPLICATIONS

This application is based upon and claims the benefit of priority from Japanese Patent Application No. 2018-234204, filed on Dec. 14, 2018; the entire contents of which are incorporated herein by reference.

FIELD

Embodiments described herein relate generally to an ultrasonic wave diagnostic apparatus, a medical information processing apparatus, and a computer program product.

BACKGROUND

Various kinds of conventionally disclosed technologies objectively and quantitatively evaluate the function of a site (for example, an organ such as the heart) of a subject by analyzing three-dimensional moving image data obtained through image capturing of the site. For example, an ultrasonic wave diagnostic apparatus evaluates the cardiac function by analyzing motion of the cardiac wall through wall motion tracking (WMT). In the WMT, for example, track processing using local region pattern matching is performed on three-dimensional moving image data of the heart collected by using an ultrasonic wave probe. Accordingly, analysis results of, for example, the myocardial strain and heart volume related to the left and right cardiac ventricles of the heart are output.

DETAILED DESCRIPTION

The embodiments is intended to provide an ultrasonic wave diagnostic apparatus, a medical information processing apparatus, and a computer program product that are capable of appropriately analyzing the size and shape of an annulus part.

An ultrasonic wave diagnostic apparatus according to an embodiment includes processing circuitry. The processing circuitry acquires a plurality of pieces of volume data obtained through image capturing of a region including the cardiac ventricle of a subject for a predetermined duration. The processing circuitry estimates motion of tissue of the cardiac ventricle by using the pieces of volume data. The processing circuitry calculates, based on a result of the estimation, cardiac ventricle information indicating at least one of wall motion information and volume information related to the cardiac ventricle. The processing circuitry calculates, based on a result of the estimation, annulus information related to the size or shape of an annulus position of a valve related to inflow or outflow of blood current at the cardiac ventricle. The processing circuitry outputs the cardiac ventricle information and the annulus information.

The following describes an ultrasonic wave diagnostic apparatus, a medical information processing apparatus, and a computer program product according to embodiments with reference to the accompanying drawings. The embodiment is not limited to the following description. The embodiments may be combined with any other embodiment or any conventional technology without causing inconsistency to the contents of processing.

First Embodiment

Figure 1:
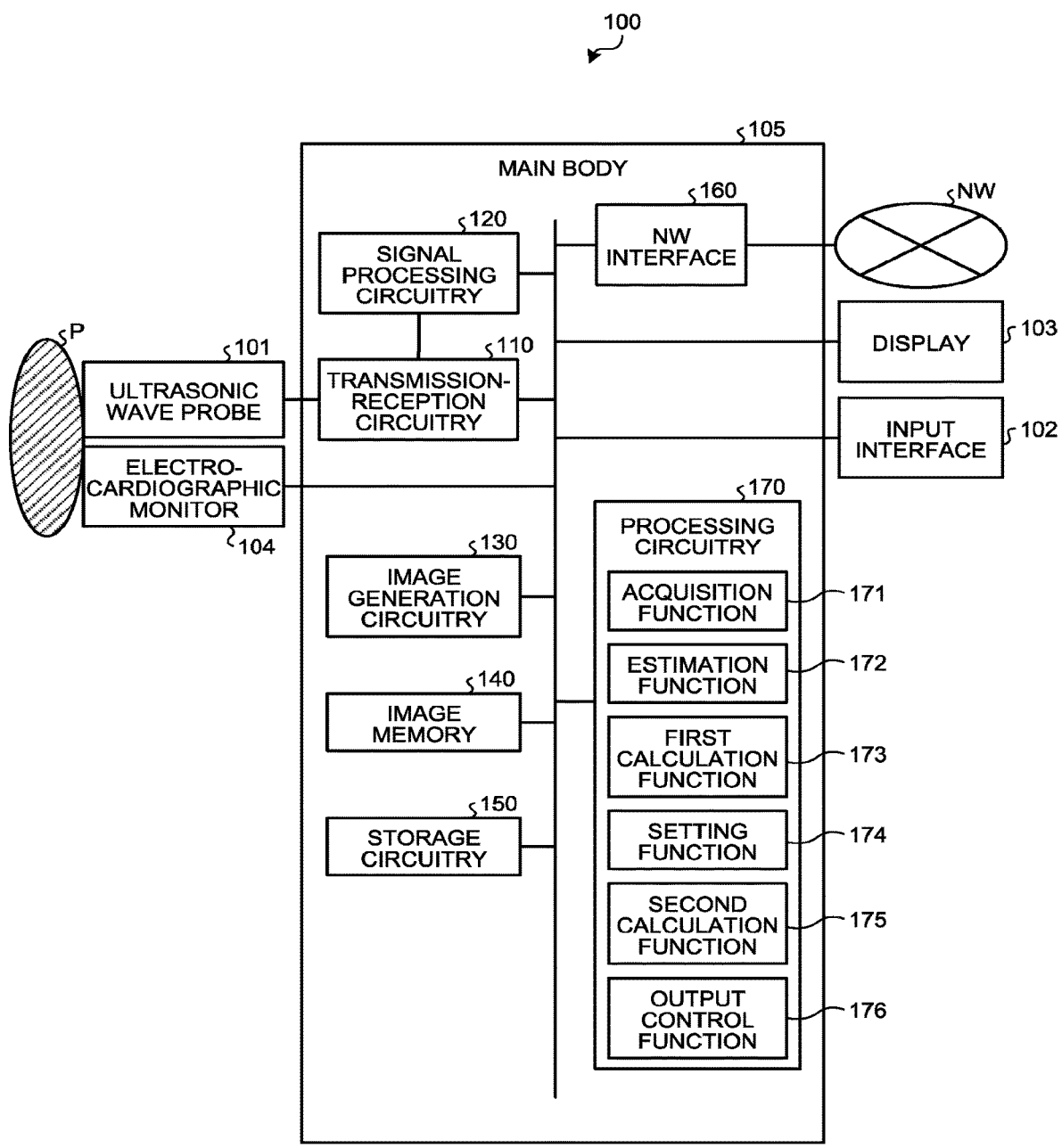
FIG. 1 is a block diagram illustrating an exemplary configuration of an ultrasonic wave diagnostic apparatus according to a first embodiment.

FIG. 1 is a block diagram illustrating an exemplary configuration of an ultrasonic wave diagnostic apparatus 100 according to a first embodiment. As illustrated in FIG. 1, the ultrasonic wave diagnostic apparatus 100 according to the first embodiment includes an ultrasonic wave probe 101, an input interface 102, a display 103, an electrocardiographic monitor 104, and a main body 105. The ultrasonic wave probe 101, the input interface 102, the display 103, and the electrocardiographic monitor 104 are each connected with the main body 105 to perform communication therebetween.

The ultrasonic wave probe 101 includes a plurality of transducer elements configured to generate ultrasonic wave based on a drive signal supplied from transmission-reception circuitry 110 included in the main body 105. The ultrasonic wave probe 101 receives reflected wave from a subject P and converts the reflected wave into an electric signal. The ultrasonic wave probe 101 also includes a matching layer provided to each transducer element, and a backing material for preventing propagation of ultrasonic wave beyond the transducer element, and the like. The ultrasonic wave probe 101 is detachably connected with the main body 105.

When ultrasonic wave is transmitted from the ultrasonic wave probe 101 to the subject P, the transmitted ultrasonic wave is sequentially reflected at discontinuous surfaces of acoustic impedance at body tissue of the subject P and received as a reflected wave signal by the transducer elements included in the ultrasonic wave probe 101. The amplitude of the received reflected wave signal depends on the difference in acoustic impedance at each discontinuous surface at which the ultrasonic wave is reflected. A reflected wave signal obtained when a transmitted ultrasonic wave pulse is reflected by blood current or a surface such as a cardiac wall, which are moving, is provided with frequency shift depending on a speed component of the moving object in the transmission direction of ultrasonic wave due to the Doppler effect.

The input interface 102 receives an input operation of various kinds of instructions and information from an operator. Specifically, the input interface 102 converts the input operation received from the operator into an electric signal and outputs the electric signal to processing circuitry 170 of the main body 105. For example, the input interface 102 is achieved by a track ball, a switch button, a mouse, a keyboard, a touch pad through which an input operation is performed by touching an operation surface, a touch screen as integration of a display screen and a touch pad, a non-contact input circuit using an optical sensor, or a voice input circuit. The input interface 102 is not limited to those including a physical operation member such as a mouse or a keyboard. Examples of the input interface 102 include an electric signal processing circuit configured to receive the electric signal corresponding to an input operation from an external input instrument provided separately from the device and configured to output the electric signal to a control circuit.

The display 103 displays various kinds of information and images. Specifically, the display 103 converts data of information and images transferred from the processing circuitry 170 into display electric signals and outputs the display electric signals. For example, the display 103 is achieved by a liquid crystal monitor, a cathode ray tube (CRT) monitor, or a touch panel. Examples of output devices included in the ultrasonic wave diagnostic apparatus 100 are not limited to the display 103 but include a speaker. For example, the speaker outputs predetermined sound such as beep sound to notify the operator of the processing status of the main body 105.

The electrocardiographic monitor 104 acquires an electrocardiogram (ECG) of the subject P as a living body signal of the subject P. The electrocardiographic monitor 104 transmits the acquired electrocardiogram to the main body 105. The present embodiment describes a case in which the electrocardiographic monitor 104 is used as a means for acquiring information related to the cardiac phase of the heart of the subject P, but the embodiments is not limited thereto. For example, the ultrasonic wave diagnostic apparatus 100 may acquire the information related to the cardiac phase of the heart of the subject P by acquiring the time of second heart sound (second sound) of a phonocardiogram or the time of aortic valve close (AVC) determined through measurement of ejection blood current of the heart based on spectrum Doppler.

The main body 105 is a device configured to generate ultrasonic wave image data based on a reflected wave signal received by the ultrasonic wave probe 101. The main body 105 illustrated in FIG. 1 is a device capable of generating two-dimensional ultrasonic wave image data based on two-dimensional reflected wave data received by the ultrasonic wave probe 101. In addition, the main body 105 is a device capable of generating three-dimensional ultrasonic wave image data based on three-dimensional reflected wave data received by the ultrasonic wave probe 101.

As illustrated in FIG. 1, the main body 105 includes the transmission-reception circuitry 110, signal processing circuitry 120, image generation circuitry 130, an image memory 140, storage circuitry 150, a network (NW) interface 160, and the processing circuitry 170. The transmission-reception circuitry 110, the signal processing circuitry 120, the image generation circuitry 130, the image memory 140, the storage circuitry 150, the NW interface 160, and the processing circuitry 170 are connected with each other to perform communication therebetween.

The transmission-reception circuitry 110 includes a pulse generator, a transmission delay unit, a pulser, and the like and supplies a drive signal to the ultrasonic wave probe 101. The pulse generator repeatedly generates a rate pulse for forming transmission ultrasonic wave at a predetermined rate frequency. In addition, the transmission delay unit provides, to each rate pulse generated by the pulse generator, a delay time for each transducer element necessary for focusing ultrasonic wave generated from the ultrasonic wave probe 101 into a beam form and determining transmission directionality. The pulser applies a drive signal (drive pulse) to the ultrasonic wave probe 101 at a timing based on the rate pulse. In other words, the transmission delay unit optionally adjusts the transmission direction of ultrasonic wave transmitted from the surface of each transducer element by changing the delay time provided to each rate pulse.

The transmission-reception circuitry 110 is capable of instantaneously changing the transmission frequency, the transmission drive voltage, and the like to execute a predetermined scan sequence based on an instruction from the processing circuitry 170. In particular, change of the transmission drive voltage is achieved by a linear-amplifier oscillation circuit capable of instantaneously switching the value of the voltage or a mechanism capable of electrically switching a plurality of power source units.

The transmission-reception circuitry 110 includes a pre-amplifier (pre-amp), an analog/digital (A/D) converter, a reception delay unit, an adder, and the like and generates reflected wave data by performing various kinds of processing on a reflected wave signal received by the ultrasonic wave probe 101. The pre-amplifier amplifies the reflected wave signal for each channel. The A/D converter performs A/D conversion of the amplified reflected wave signal. The reception delay unit provides a delay time necessary for determining reception directionality. The adder generates reflected wave data by performing addition processing on the reflected wave signal processed by the reception delay unit. Through the addition processing at the adder, a reflection component from a direction in accordance with the reception directionality of the reflected wave signal is enhanced, and a comprehensive beam of ultrasonic wave transmission and reception is formed based on the reception directionality and the transmission directionality.

The form of an output signal from the transmission-reception circuitry 110 may be selected from among various kinds of forms such as a radio frequency (RF) signal including phase information or amplitude information after envelope detection processing.

The signal processing circuitry 120 receives the reflected wave data from the transmission-reception circuitry 110, and performs logarithmic amplification, envelope detection processing, and the like on the reflected wave data to generate data (B mode data) in which the signal intensity is expressed in brightness as luminance. In addition, the signal processing circuitry 120 performs frequency analysis on speed information from the reflected wave data received from the transmission-reception circuitry 110 to extract blood current, tissue, and contrast dye echo (echo) components due to the Doppler effect, thereby generating data (Doppler data) in which moving object information such as speed, dispersion, and power is extracted for multiple points.

The signal processing circuitry 120 exemplarily illustrated in FIG. 1 can process two-dimensional reflected wave data and three-dimensional reflected wave data. Specifically, the signal processing circuitry 120 generates two-dimensional B mode data from the two-dimensional reflected wave data, and generates three-dimensional B mode data from the three-dimensional reflected wave data. In addition, the signal processing circuitry 120 generates two-dimensional Doppler data from the two-dimensional reflected wave data, and generates three-dimensional Doppler data from the three-dimensional reflected wave data.

The image generation circuitry 130 generates ultrasonic wave image data from the data generated by the signal processing circuitry 120. Specifically, the image generation circuitry 130 generates two-dimensional B mode image data in which the intensity of reflected wave is expressed in luminance from the two-dimensional B mode data generated by the signal processing circuitry 120. In addition, the image generation circuitry 130 generates two-dimensional Doppler image data indicating the moving object information from the two-dimensional Doppler data generated by the signal processing circuitry 120. The two-dimensional Doppler image data is a speed image, a dispersion image, a power image, or an image obtained by combining these images. In addition, the image generation circuitry 130 may generate M mode image data from temporally sequential data of the B mode data on one scanning line, which is generated by the signal processing circuitry 120. In addition, the image generation circuitry 130 may generate, from the Doppler data generated by the signal processing circuitry 120, a Doppler waveform obtained by plotting speed information of blood current and tissue in a temporally sequential manner.

The image generation circuitry 130 typically generates display ultrasonic wave image data through conversion (scan conversion) of a scanning line signal string of ultrasonic wave scanning into a scanning line signal string in a video format such as a television format. Specifically, the image generation circuitry 130 generates display ultrasonic wave image data by performing coordinate transform in accordance with the form of ultrasonic wave scanning by the ultrasonic wave probe 101. In addition, the image generation circuitry 130 performs various kinds of image processing other than scan conversion, such as image processing (smoothing processing) of regenerating an averaged luminance value image by using a plurality of image frames after scan conversion, and image processing (edge enhancement processing) using a differential filter in an image. In addition, the image generation circuitry 130 synthesizes the ultrasonic wave image data with character information, scales, body marks, and the like of various kinds of parameters.

In addition, the image generation circuitry 130 performs rendering processing on volume data to generate various kinds of two-dimensional image data for displaying the volume data on the display 103. The rendering processing performed by the image generation circuitry 130 is, for example, processing of generating MPR sectional image data from the volume data by performing multi planer reconstruction (MPR). Alternatively, the rendering processing performed by the image generation circuitry 130 is, for example, processing of performing "curved MPR" on the volume data or processing of performing "maximum intensity projection" on the volume data. Other examples of the rendering processing performed by the image generation circuitry 130 include volume rendering (VR) processing and surface rendering (SR) processing.

Specifically, B mode data and Doppler data are ultrasonic wave image data before scan conversion processing, and data generated by the image generation circuitry 130 is display ultrasonic wave image data after scan conversion processing. B mode data and Doppler data are also called raw data. The image generation circuitry 130 generates "two-dimensional B mode image data and two-dimensional Doppler image data" as two-dimensional ultrasonic wave image data for display from "two-dimensional B mode data and two-dimensional Doppler data" as two-dimensional ultrasonic wave image data before scan conversion processing.

The image memory 140 stores display image data generated by the image generation circuitry 130. The image memory 140 may also store data generated by the signal processing circuitry 120. For example, B mode data and Doppler data stored in the image memory 140 can be read by the operator after diagnosis, and becomes display ultrasonic wave image data through the image generation circuitry 130 in that case.

The image generation circuitry 130 stores ultrasonic wave image data and a time of ultrasonic wave scanning performed to generate the ultrasonic wave image data in the image memory 140 in association with an electrocardiogram transmitted from the electrocardiographic monitor 104. The processing circuitry 170 to be described later can refer to the data stored in the image memory 140 to acquire the cardiac phase at the ultrasonic wave scanning performed to generate the ultrasonic wave image data.

The storage circuitry 150 stores various kinds of data. For example, the storage circuitry 150 stores various kinds of data such as control programs for performing ultrasonic wave transmission and reception, image processing, and display processing, diagnosis information (for example, a patient ID and observation by a doctor), diagnosis protocols, and various body marks. The storage circuitry 150 is also used for, for example, storage of image data stored in the image memory 140 as necessary. The storage circuitry 150 is achieved by, for example, a semiconductor memory element such as a random access memory (RAM) or a flash memory, a hard disk (HDD), or an optical disk. The data stored in the storage circuitry 150 can be forwarded to an external device through the NW interface 160. The external device is, for example, a personal computer (PC) or tablet terminal used by a doctor who performs image diagnosis, a storage device storing images, or a printer.

The NW interface 160 controls communication performed between the main body 105 and the external device. Specifically, the NW interface 160 receives various kinds of information from the external device, and outputs the received information to the processing circuitry 170. The NW interface 160 is achieved by, for example, a network card, a network adapter, or a network interface controller (NIC).

The first embodiment describes a case in which the ultrasonic wave diagnostic apparatus 100 is connected with the external device (such as an information processing apparatus or a storage device) through a network NW to perform communication therebetween, but is not limited thereto. For example, the ultrasonic wave diagnostic apparatus 100 can perform information transfer with the external device not through the network NW but through a storage medium, a removable storage device (such as an external HDD device), or the like.

The processing circuitry 170 controls the entire processing at the ultrasonic wave diagnostic apparatus 100. Specifically, the processing circuitry 170 controls processing at the transmission-reception circuitry 110, the signal processing circuitry 120, and the image generation circuitry 130 based on various setting requests input by the operator through the input interface 102, and various kinds of control programs and various kinds of data read from the storage circuitry 150. The processing circuitry 170 also controls the display 103 to display display ultrasonic wave image data stored in the image memory 140 and the storage circuitry 150.

The processing circuitry 170 executes an acquisition function 171, an estimation function 172, a first calculation function 173, a setting function 174, a second calculation function 175, and an output control function 176. The acquisition function 171 is an exemplary acquisition unit. The estimation function 172 is an exemplary estimation unit. The first calculation function 173 is an exemplary first calculation unit. The setting function 174 is an exemplary setting unit. The second calculation function 175 is an exemplary second calculation unit. The output control function 176 is an exemplary output control unit. The contents of processing at the acquisition function 171, the estimation function 172, the first calculation function 173, the setting function 174, the second calculation function 175, and the output control function 176 executed by the processing circuitry 170 will be described later.

For example, processing functions executed by the acquisition function 171, the estimation function 172, the first calculation function 173, the setting function 174, the second calculation function 175, and the output control function 176 as components of the processing circuitry 170 illustrated in FIG. 1 are recorded in the form of computer-executable computer program in the storage circuitry 150. The processing circuitry 170 is a processor configured to achieve the function corresponding to each computer program by reading the computer program from the storage circuitry 150 and executing the computer program. In other words, the processing circuitry 170 having read each computer program has the corresponding function indicated in the processing circuitry 170 in FIG. 1.

Each processing function described below is achieved by the single processing circuitry 170 in the present embodiment described below, but the processing circuitry may be configured by combining a plurality of independent processors, and the function may be achieved by each processor executing a computer program.

The configuration of the ultrasonic wave diagnostic apparatus 100 according to the first embodiment is described above. With such a configuration, the ultrasonic wave diagnostic apparatus 100 appropriately analyzes the size and shape of an annulus part by executing processing described below.

The following description will be made on a case in which wall motion of the right cardiac ventricle is analyzed by the ultrasonic wave diagnostic apparatus 100 through wall motion tracking (WMT) using a three-dimensional image, but wall motion of the left cardiac ventricle may be analyzed.

The acquisition function 171 acquires a plurality of pieces of volume data obtained through image capturing of a region including a cardiac ventricle of the subject P for at least one cardiac cycle (predetermined duration). For example, the acquisition function 171 acquires a plurality of pieces of volume data obtained through image capturing of a region including the right cardiac ventricle as the cardiac ventricle of the subject P.

For example, the operator performs image capturing of moving image data of three-dimensional ultrasonic wave image data in which myocardium is delineated by performing three-dimensional scanning of the region including the right cardiac ventricle of the subject P by using the ultrasonic wave probe 101. The moving image data is, for example, an ultrasonic wave image data group including ultrasonic wave image data collected as a B mode luminance signal for each phase. The "phase" means an optional time point (timing) in periodic motion of the heart and is also referred to as "cardiac phase".

Then, the image generation circuitry 130 generates moving image data of the right cardiac ventricle of the heart, and stores the generated moving image data in the image memory 140. Then, the operator sets, as a processing target interval, for example, the interval of one heartbeat from R wave to the next R wave in an electrocardiogram. The present embodiment is also applicable to a case in which the processing target interval is set to be the interval of two heartbeats or the interval of three heartbeats.

Then, the acquisition function 171 reads, for example, an ultrasonic wave image data group from the image memory 140. The ultrasonic wave image data group includes three-dimensional ultrasonic wave image data (volume data) of a plurality of frames included in the interval of one heartbeat set by the operator.

The estimation function 172 estimates motion of tissue of the cardiac ventricle by using a plurality of pieces of volume data. For example, the estimation function 172 estimates motion information of tissue of the right cardiac ventricle through three-dimensional WMT (3DWMT).

First, the estimation function 172 sets an initial outline to a target site (the right cardiac ventricle) included in the volume data through a processing procedure as described below. The region of the right cardiac ventricle is defined by a boundary site from a region other than the right cardiac ventricle. In the present embodiment, the boundary site is a "tubal inflow part including the tricuspid annulus: Inlet" through which blood flows into the right cardiac ventricle, and a "tubal outflow part including the pulmonary artery annulus: RVOT" through which blood flows out of the right cardiac ventricle.

For example, the operator specifies an optional cardiac phase for temporally sequential volume data acquired by the acquisition function 171. The specified optional cardiac phase is an optional frame among frames included in the interval of one heartbeat and is preferably, for example, the end-diastolic phase (first R wave phase). Then, when the optional cardiac phase is specified by the operator, the estimation function 172 sets a three-dimensional initial outline to ultrasonic wave image data in the specified cardiac phase.

The three-dimensional initial outline is generated through, for example, interpolation processing of two-dimensional outline lines input for a plurality of reference MPR sections. For example, the operator inputs, for each reference MPR section, an outline line indicating the outline of the endocardium of the right cardiac ventricle. Then, the estimation function 172 converts the position of the outline line input for each reference MPR section into the coordinates of three-dimensional ultrasonic wave image data. Then, the estimation function 172 generates a three-dimensional outline shape (initial outline) with the outline lines in the three-dimensional ultrasonic wave image data through spatial interpolation processing on the outline lines. In this manner, the estimation function 172 sets the initial outline of the endocardium of the right cardiac ventricle. The initial outline of the epicardium of the right cardiac ventricle is preferably set at a position apart from the endocardial surface by a predetermined wall thickness (4 to 6 mm approximately).

Figure 2:
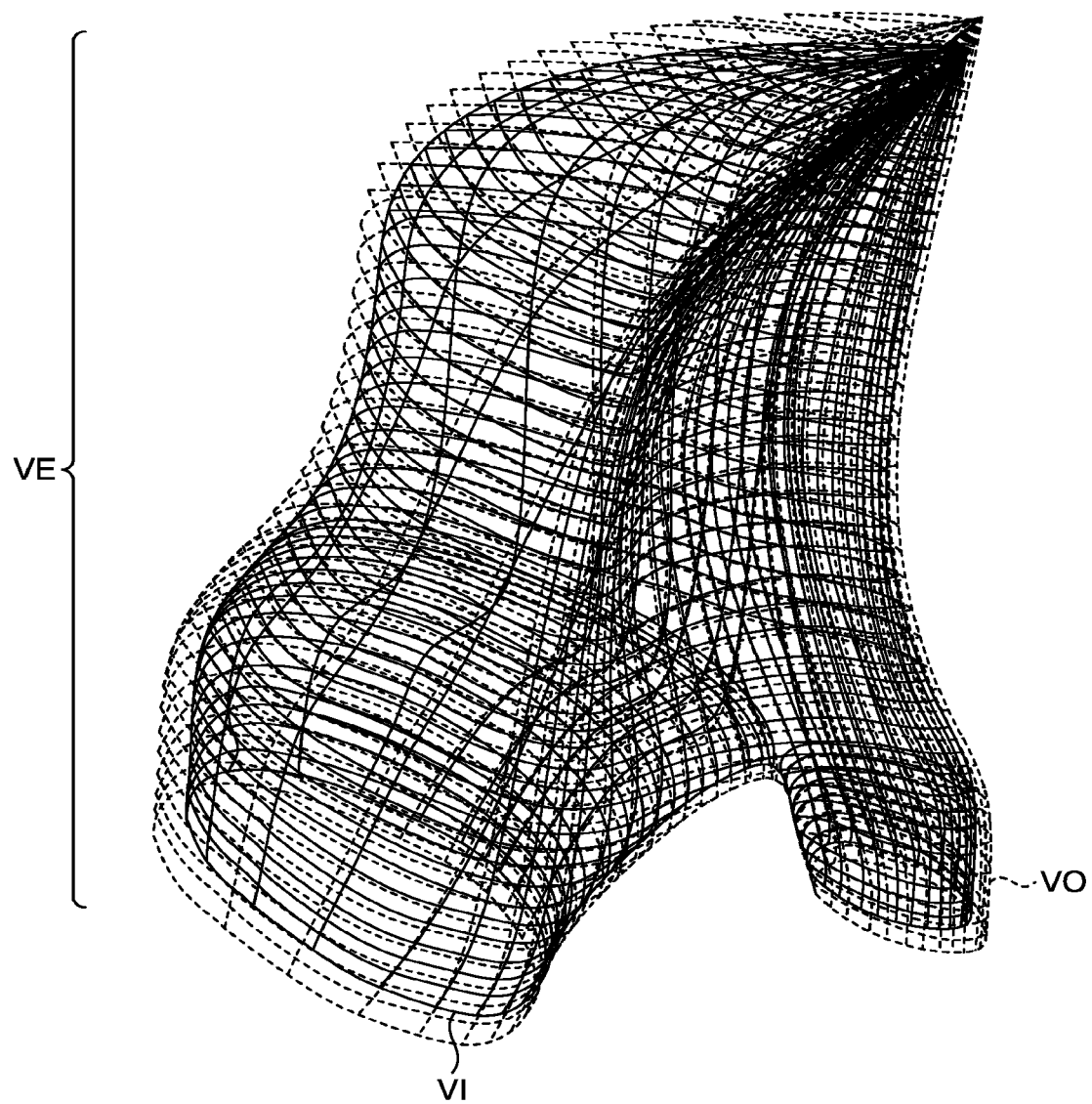
FIG. 2 is a diagram for description of an initial outline set by an estimation function according to the first embodiment.

FIG. 2 is a diagram for description of the initial outline set by the estimation function 172 according to the first embodiment. FIG. 2 exemplarily illustrates an initial outline (VE) set to the right cardiac ventricle. In FIG. 2, a mesh structure illustrated with solid lines corresponds to an initial outline (VI) set to the endocardium of the right cardiac ventricle, and a mesh structure illustrated with dashed lines corresponds to an initial outline (VO) set to the epicardium of the right cardiac ventricle.

As illustrated in FIG. 2, the estimation function 172 sets the three-dimensional initial outline (VE) at a position corresponding to the endocardium of the right cardiac ventricle among ultrasonic wave image data in the initial phase. The initial phase may be an optional cardiac phase but is preferably the end-diastole (ED) phase. Each mesh intersection point in the initial outline (VE) is a "component point" included in the inner outline or outer outline of the right cardiac ventricle. The component point corresponds to a tracking point temporally tracked for calculating tissue motion information.

Then, the estimation function 172 sets address numbers to a plurality of positions on the initial outline. For example, the estimation function 172 sets address numbers to a plurality of tracking points included in the set initial outline (VE). Each address number is provided to identify a tracking point and defined based on, for example, the position of a tracking point on the endocardium of the heart. The address number is not limited to a number (numerical value) but may be identification information such as a character or a symbol with which the position of each tracking point is identifiable.

For example, the estimation function 172 defines P_endo (t, h, d) to be the position of each tracking point on the endocardium of the heart. In the definition, t represents a frame (cardiac phase) included in the interval of one heartbeat, h represents an address number in the longitudinal direction (height), and d represents an address number in the circumferential direction (azimuth). Specifically, the estimation function 172 sets t=0 at ED phase as the initial phase. In addition, the estimation function 172 sets a reference position in the circumferential direction to be, for example, an end part of the right cardiac ventricle on the tricuspid valve side, and sets d of a tracking point at the position to be zero. Accordingly, the position of the tracking point at the reference position is expressed as P_endo(0, h, 0). Then, the estimation function 172 sequentially sets the address number d=0, 1, 2, 3, . . . to tracking points in the circumferential direction from the tracking point at the reference position. In addition, the estimation function 172 sets a reference position in the longitudinal direction to be the position of an annular outline farthest from a heart apex part in the three-dimensional initial outline, and sets h of a tracking point at the position to be zero. Accordingly, the position of the tracking point at the reference position is expressed as P_endo(0, 0, d). Then, the estimation function 172 sequentially sets the address number h=0, 1, 2, 3 . . . to tracking points on the heart apex side on the tracking point at the reference position.

In this manner, the estimation function 172 sets a plurality of tracking points (component points) provided with the address numbers at the position corresponding to the endocardium of the right cardiac ventricle in the volume data. The setting of the initial outline is not limited to the above-described manual operation, but the estimation function 172 may automatically or semi-automatically detect any boundary in the image by using a database of endocardial outline shapes (for example, a statistical database of outlines set in the past).

For example, the estimation function 172 performs track processing including pattern matching by using volume data in the initial phase in which a plurality of tracking points are set and volume data in the next phase, thereby tracking the positions of a plurality of tracking points in a plurality of pieces of ultrasonic wave image data included in a volume data group.

For example, when a plurality of tracking points are set at the position corresponding to the initial outline for volume data of frame t=0 included in the volume data group, the estimation function 172 tracks the position of each tracking point in another frame t through processing including pattern matching. Specifically, the estimation function 172 repeatedly performs pattern matching on volume data of a frame for which a plurality of tracking points are already set and volume data of a frame adjacent to the frame, specifically, the estimation function 172 tracks the position of each tracking point P_endo(t, h, d) in volume data of frames at t=0, 1, 2, 3 . . . , starting with each tracking point P_endo(0, h, d) on the endocardium of the heart in volume data of t=0. As a result, the estimation function 172 obtains coordinate information of each tracking point included in the endocardium of the heart for each frame included in the interval of one heartbeat.

Then, the estimation function 172 calculates motion information indicating tissue motion for each ultrasonic wave image data by using the positions of the tracking points in the pieces of ultrasonic wave image data included in the volume data group. The motion information calculated by the estimation function 172 is provided to each tracking point used in the calculation. Specifically, for example, the motion information calculated from each tracking point on the endocardium of the heart is defined as V_endo(t, h, d). Then, the estimation function 172 stores the calculated motion information in the image memory 140.

In this manner, the estimation function 172 estimates the motion information by temporally tracking a plurality of tracking points disposed along the outline of the cardiac ventricle. The above description is made with the example of processing on the endocardium of the right cardiac ventricle, but the embodiment is not limited thereto. For example, the above-described processing may be executed not only on the endocardium but also on the epicardium or an intermediate layer between the endocardium and the epicardium. The estimation function 172 may execute the processing not only for the right cardiac ventricle but also for an optional predetermined region such as the left cardiac ventricle, the left atrium, the right atrium, or the entire heart.

The first calculation function 173 calculates, based on a result of the estimation by the estimation function 172, the first calculation information including at least one of wall motion information and volume information related to the cardiac ventricle. For example, the first calculation function 173 calculates, as the wall motion information, at least one of displacement in a predetermined direction, strain in a predetermined direction, and an area change ratio that are entirely or locally defined for the right cardiac ventricle. The first calculation information is also called cardiac ventricle information. The cardiac ventricle information indicates at least one of the wall motion information and the volume information related to the cardiac ventricle.

Specifically, the first calculation function 173 calculates, as the wall motion information, for example, local myocardial displacement [mm] of each tracking point per frame, local myocardial strain [%] as the change rate of the distance between two points, or local myocardial speed [cm/s] and local myocardial strain rate [1/s] as temporal changes of the displacement and the strain. However, the wall motion information is not limited to these parameters but may be any parameter that can be calculated by using coordinate information of a plurality of tracking points in each frame.

For example, the wall motion information may be provided with component separation. In a case of the right cardiac ventricle, for example, indexes such as longitudinal strain (LS) obtained through component separation in the longitudinal direction and circumferential strain (CS) obtained through component separation in the circumferential direction are used. These indexes are calculated by a two-dimensional speckle tracking method using a two-dimensional image (apical view or short-axis view) of the right cardiac ventricle or by three-dimensional speckle tracking method using a three-dimensional image. In the three-dimensional speckle tracking method, a local area change ratio (AC) may be defined. Component separation is unnecessary for AC, and thus reliable analysis is possible for a complicate shape like that of the right cardiac ventricle.

Examples of wall motion information clinically well used for function evaluation of the right cardiac ventricle include TAPSE (tricuspid annulus contraction phase moving amount) measured in an M mode. The M mode is one-dimensional analysis, and thus in the TAPSE, a displacement component toward the ultrasonic wave probe 101 is observed for a part near the tricuspid annulus. However, with the three-dimensional speckle tracking method, displacement information for the entire region of the right cardiac ventricle can be obtained. The direction of displacement in this case may not be with respect to the ultrasonic wave probe 101, but displacement components in the longitudinal direction and the wall thickness (radial) direction with respect to the right cardiac ventricle may be detected. A travel distance D ($D=\text{sqrt}((Px(n)-Px(n0))^2+(Py(n)-Py(n0))^2+(Pz(n)-Pz(n0))^2)$) for which component separation in a direction is not performed may be used as an index unlikely to depend on the complicate shape of the right cardiac ventricle. In the above expression, ($Px(n)$, $Py(n)$, $Pz(n)$) represents the position of a tracking point P, and n represents a phase, and n0 represents reference phase.

The first calculation function 173 calculates volume information as an index for the pump function of the heart. For example, the first calculation function 173 calculates, as the volume information, the volume of the cardiac cavity and a three-dimensional region surrounded by a valve site (boundary position). Accordingly, the first calculation function 173 calculates the end-diastolic volume (EDV), the end-systolic volume (ESV), the ejection fraction (EF), and the like. The cardiac phase and the region when the first calculation function 173 calculates the volume information may be change as appropriate.

In this manner, the first calculation function 173 calculates the wall motion information and/or the volume information related to the right cardiac ventricle as the first calculation information based on the result of the estimation by the estimation function 172. The wall motion information and the volume information calculated by the first calculation function 173 are not limited to the above-described examples, but any well-known parameter may be calculated. The kind of a parameter calculated by the first calculation function 173 may be preset or may be selected by the operator as appropriate.

The setting function 174 sets a region of interest (ROI) corresponding to an annulus position of a valve related to inflow or outflow of blood current in the cardiac ventricle. For example, the setting function 174 sets the region of interest at a position corresponding to at least one of the tricuspid annulus and the pulmonary artery annulus as the annulus position.

Figure 3:
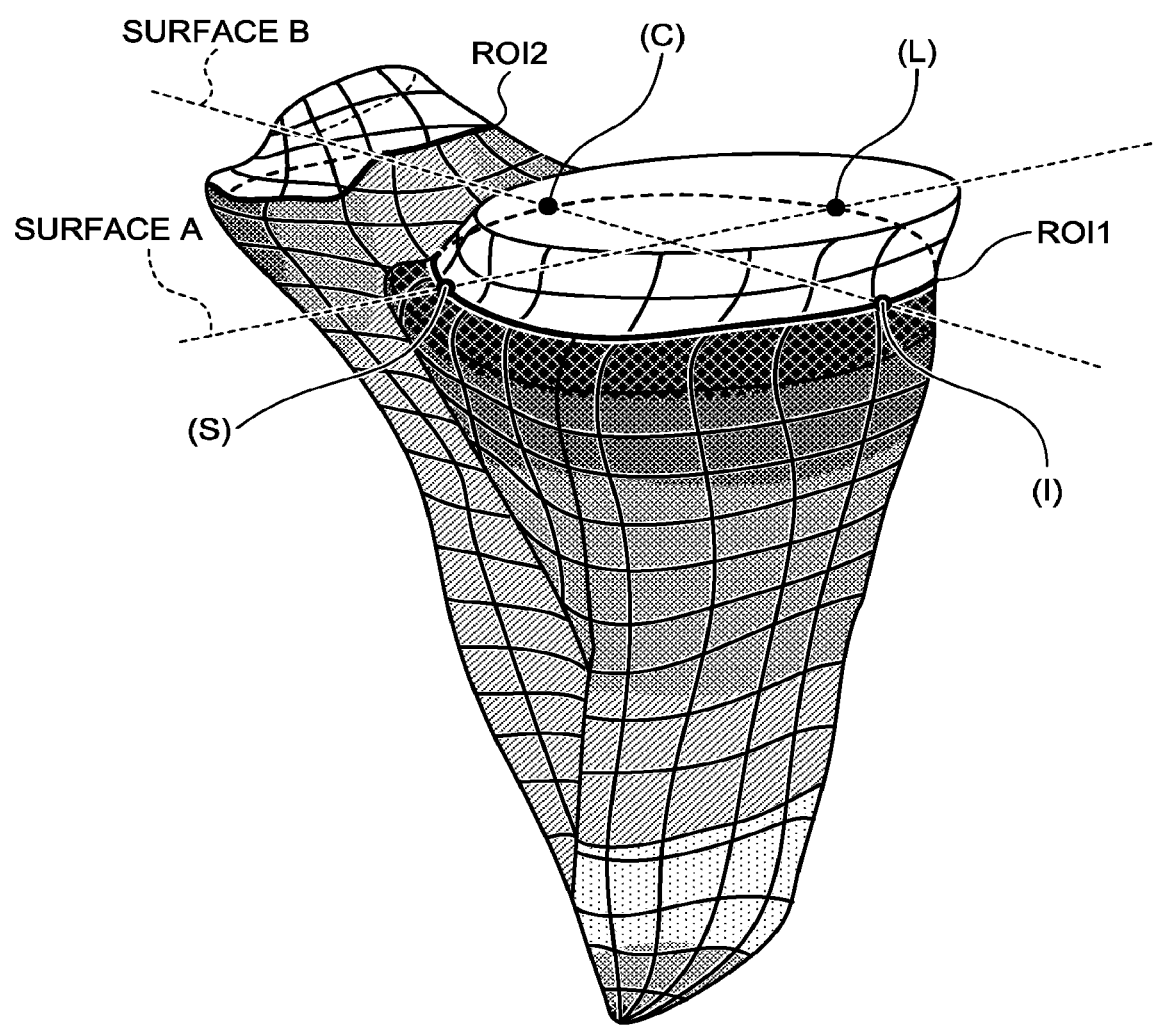
FIG. 3 is a diagram for description of processing performed by a setting function according to the first embodiment.
Figure 4:
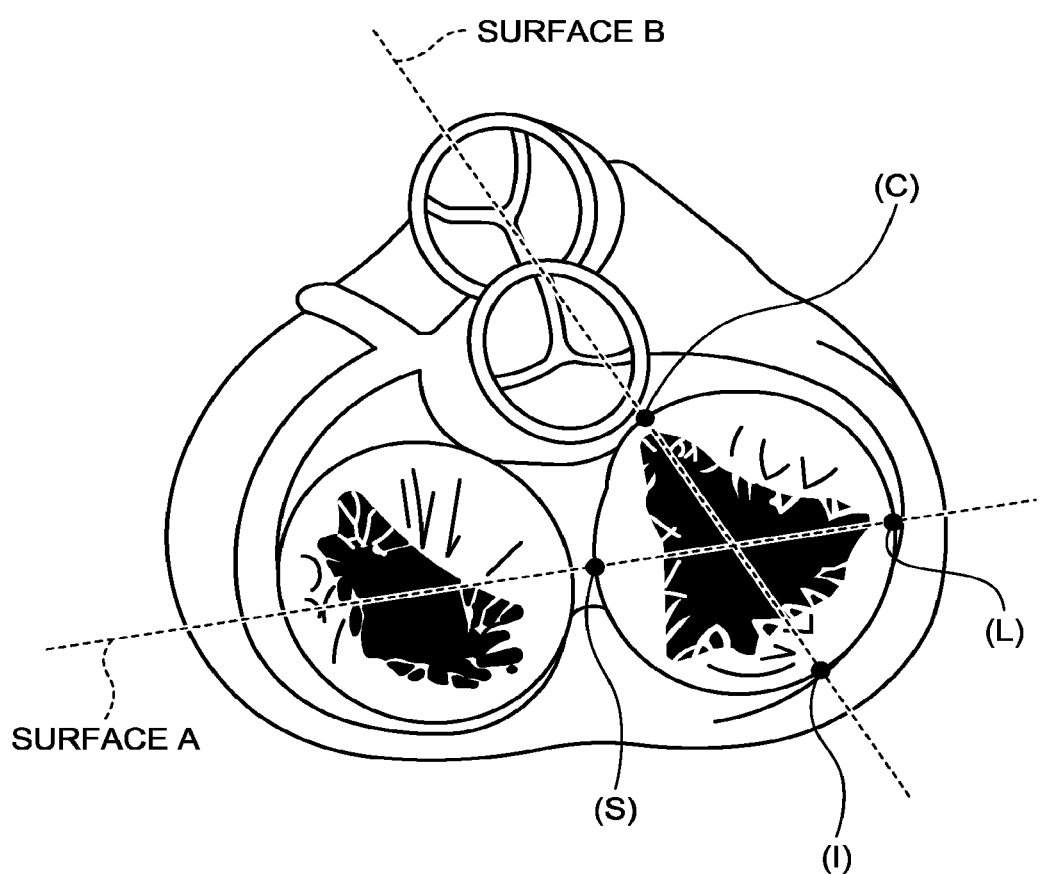
FIG. 4 is a diagram for description of the processing performed by the setting function according to the first embodiment.

FIGS. 3 and 4 are diagrams for description of processing performed by the setting function 174 according to the first embodiment. FIG. 3 exemplarily illustrates a rendering image obtained by performing surface rendering processing on the inner outline (endocardial surface) of the right cardiac ventricle. FIG. 4 exemplarily illustrates a cross-sectional view at the annulus position (annulus level) when the cardiac ventricle side (foot side) is viewed from the atrium side (head side). The rendering image illustrated in FIG. 3 is generated by, for example, a technology disclosed in Japanese Patent Laid-open No. 2016-093302 (hereinafter referred to as "Patent Literature 1"). Each mesh intersection point on the rendering image corresponds to a tracking point disposed on the inner outline of the right cardiac ventricle. In addition, colors in accordance with optional wall motion information described above are mapped on the rendering image.

For example, the setting function 174 sets the region of interest by receiving specification of the position (point) of the annulus part on a sectional image from the operator. To specify the position of the tricuspid annulus (Inlet), as illustrated in FIGS. 3 and 4, the operator specifies two points of an annulus position (S) on the septum side on a sectional image corresponding to Surface A (A4C image) as a reference section and an annulus position (L) on the sidewall side. In addition, the operator specifies two points of an annulus position (I) on the lower wall side and an annulus position (C) on the supraventricular crest side on a sectional image corresponding to Surface B (coronal image). Then, the setting function 174 sets a curve ROI1 by linearly or non-linearly interpolating the four points of the annulus positions (S), (L), (I), and (C) specified by the operator. Since it is known that the annulus part has a saddle shape, the interpolation processing is preferably performed along the shape.

In this manner, the setting function 174 sets ROI1 at a boundary position corresponding to the tricuspid annulus. Through the same processing, the setting function 174 sets ROI2 at an annular boundary position corresponding to the pulmonary artery annulus (RVOT).

FIGS. 3 and 4 illustrate the case in which the region of interest corresponding to the tricuspid annulus is set by using two sectional images (Surfaces A and B), but the embodiment is not limited thereto. For example, the setting function 174 may set the region of interest by using optional three or more sectional images or may set the region of interest by using optional one sectional image.

For example, the technology disclosed in Patent Literature 1 is applicable as processing of setting and changing an annular boundary position. Specifically, the setting function 174 may directly set, as ROI1 and ROI2, an end part (end part on the atrium side) of the initial outline set by the estimation function 172. Alternatively, for each of ROI1 and ROI2 set to be the end part of the initial outline, the setting function 174 may receive an input operation to change an annular level from the operator and may change the annular level in accordance with the received input operation.

The second calculation function 175 calculates second calculation information related to the size of the region of interest based on the result of the estimation by the estimation function 172. For example, the second calculation function 175 calculates the second calculation information based on the positions (coordinate information) of a plurality of tracking points included in the region of interest among a plurality of tracking points. The second calculation function 175 calculates, as the second calculation information for each cardiac phase, at least one parameter among the annulus diameter at a predetermined position, the annulus perimeter, the cross-sectional area of the annulus part, and the mean annulus diameter. The second calculation information is also called annulus information. The annulus information is information related to the size or shape of the annulus position.

The following sequentially describes examples in which the annulus diameter at a predetermined position, the annulus perimeter, the cross-sectional area of the annulus part, and the mean annulus diameter are calculated for ROI1 corresponding to the tricuspid annulus. The annulus diameter at a predetermined position, the annulus perimeter, the cross-sectional area of the annulus part, and the mean annulus diameter are exemplary "annulus size information".

The following first describes calculation of "the annulus diameter at a predetermined position". For example, the second calculation function 175 calculates the annulus diameter at the position of the region of interest on an MPR sectional image specified by the operator. For example, the second calculation function 175 calculates, as an annulus diameter "iDia_A", the distance between the two points of the annulus position (S) on the septum side and the annulus position (L) on the sidewall side that are set on a sectional image Corresponding to Surface A. In addition, the second calculation function 175 calculates, as an annulus diameter "iDia_B", the distance between the two points of the annulus position (I) on the lower wall side and the annulus position (C) on the supraventricular crest side that are set on a sectional image corresponding to Surface B. The distance between two points can be calculated as, for example, the positional difference between tracking points in 3DWMT.

The annulus diameter "iDia_A" and the annulus diameter "iDia_B" can be defined in each cardiac phase "t", and thus can be calculated as functions indicating temporal change. Specifically, the second calculation function 175 sets two tracking points corresponding to the annulus position (S) on the septum side and the annulus position (L) on the sidewall side, respectively, in the initial phase "t=0" in 3DWMT. Then, the second calculation function 175 calculates the distance between the two points while tracking the positions of the two tracking points thus set in each cardiac phase "t", thereby acquiring the annulus diameter "iDia_A(t)". Through the same processing, the second calculation function 175 acquires the annulus diameter "iDia_B(t)".

The operator can adjust section positions corresponding to Surface A and Surface B separately from each other. Each section position is preferably changed through rotation about a central axis (intersection point between Surface A and Surface B). Each time each section position is changed by the operator, the second calculation function 175 calculates the annulus diameter at the changed section position. Accordingly, the operator can change the positions of the two points for calculating the annulus diameter while checking the MPR sectional image.

The following describes calculation of "the annulus perimeter". For example, the second calculation function 175 calculates a length "CL" along the annular annulus position. The length "CL" can be calculated as, for example, the sum of the distance between each pair of a plurality of tracking points included in the region of interest.

Specifically, the second calculation function 175 specifies a plurality of tracking points included in ROI1 among a plurality of tracking points set in 3DWMT. Then, the second calculation function 175 calculates the distance between each pair of adjacent tracking points among the specified tracking points, and calculates the sum of each calculated distance as the length "CL". The length "CL" can be defined in each cardiac phase "t", and thus the second calculation function 175 calculates the length "CL" for each cardiac phase "t", thereby acquiring the length "CL(t)".

The following describes calculation of "the cross-sectional area of the annulus part". For example, the second calculation function 175 calculates the cross-sectional area of the annulus part as a curved surface by using the barycenter position of a plurality of tracking points included in the region of interest and the position of each tracking point.

The shape of the annulus part is a three-dimensional curved surface shape that can dynamically change in accordance with the cardiac phase "t", and thus annulus cross-sectional area "iAreA(t)" is defined, for example, as described below. First, the second calculation function 175 specifies a plurality of tracking points (tracking point group) "CP(t, i)" included in ROI1 corresponding to the annulus part in the cardiac phase "t". The index "i" corresponds to the number (1 to N) of tracking points included in ROI1. Then, the second calculation function 175 calculates a barycenter "G(t)" of the tracking point group "CP(t, i)". Then, the second calculation function 175 calculates area "s(t, i)" of a triangle formed by a tracking point "CP(t, i)" and a tracking point "CP(t, i+1)" as a pair of adjacent tracking points and the barycenter "G(t)". The area "s(t, i)" of the triangle is preferably calculated by, for example, Heron's formula. Then, the second calculation function 175 adds the calculated areas "s(t, i)" of all (N) triangles, thereby calculating the annulus cross-sectional area "iAreA(t)= [SIGMA]s(t, i)".

The following describes calculation of "the mean annulus diameter". For example, the second calculation function 175 calculates the mean annulus diameter based on an assumption that the cross-sectional area of the annulus part is equal to the area of a circle.

For example, the second calculation function 175 calculates a mean annulus diameter "iDia_mean(t)" by using a radius "R(t)" satisfying the annulus cross-sectional area "iAreA(t)=πR(t)^2". Accordingly, the mean annulus diameter is defined by "iDia_mean(t)=2*R(t)=2*sqrt(iAreA(t)/π)". The second calculation function 175 may calculate the mean value of the annulus diameter "iDia_A(t)" and the annulus diameter "iDia_B(t)" as the mean annulus diameter "iDia_mean(t)".

In this manner, the second calculation function 175 calculates, for each cardiac phase based on the result of the estimation by the estimation function 172, at least one parameter among the annulus diameter at a predetermined position, the annulus perimeter, the cross-sectional area of the annulus part, and the mean annulus diameter. For example, the second calculation function 175 calculates the annulus information based on the estimation result at a plurality of tracking points included in the annulus position. For example, the second calculation function 175 calculates the annulus information for each of a plurality of phases included in a predetermined duration.

The above description is made with the case in which the second calculation information is calculated for ROI1 corresponding to the tricuspid annulus, but the embodiment is not limited thereto. For example, the second calculation function 175 may calculate the second calculation information for ROI2 corresponding to the pulmonary artery annulus.

The above description is made with the case in which each parameter calculated by the second calculation function 175 is calculated as dynamic information in a plurality of cardiac phases "t", but the embodiment is not limited thereto, and the parameter may be calculated as static information for an optional time phase. Each parameter calculated by the second calculation function 175 is not limited to the above-described definition but may be optionally defined by using tracking points.

The output control function 176 outputs the first calculation information and the second calculation information. For example, the output control function 176 outputs the second calculation information as at least one piece of information among a temporal change curve, a value in a predetermined cardiac phase, the maximum value in one cardiac cycle, and the minimum value in one cardiac cycle.

Figure 5:
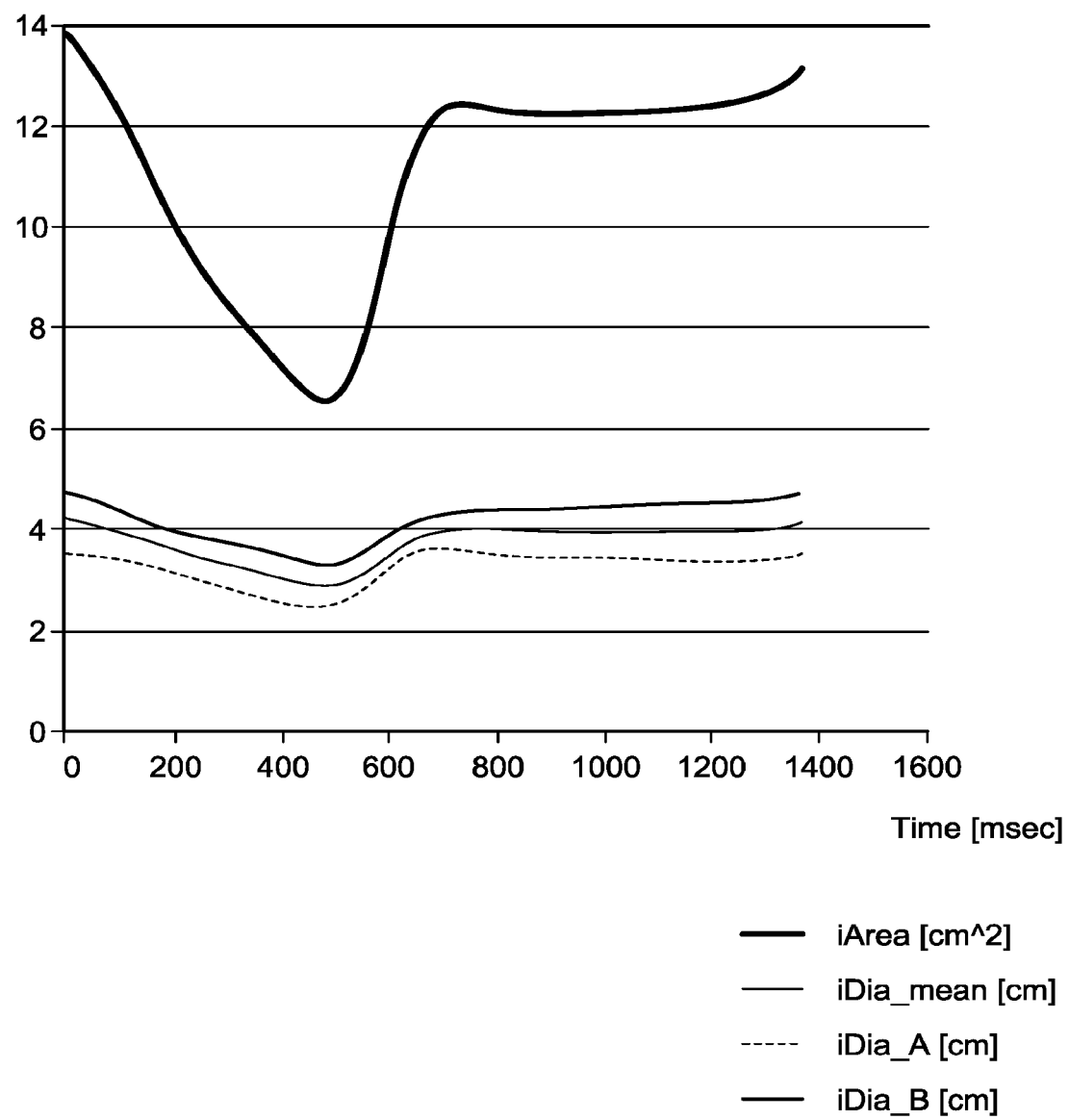
FIG. 5 is a diagram for description of processing performed by an output control function according to the first embodiment.
Figure 6:
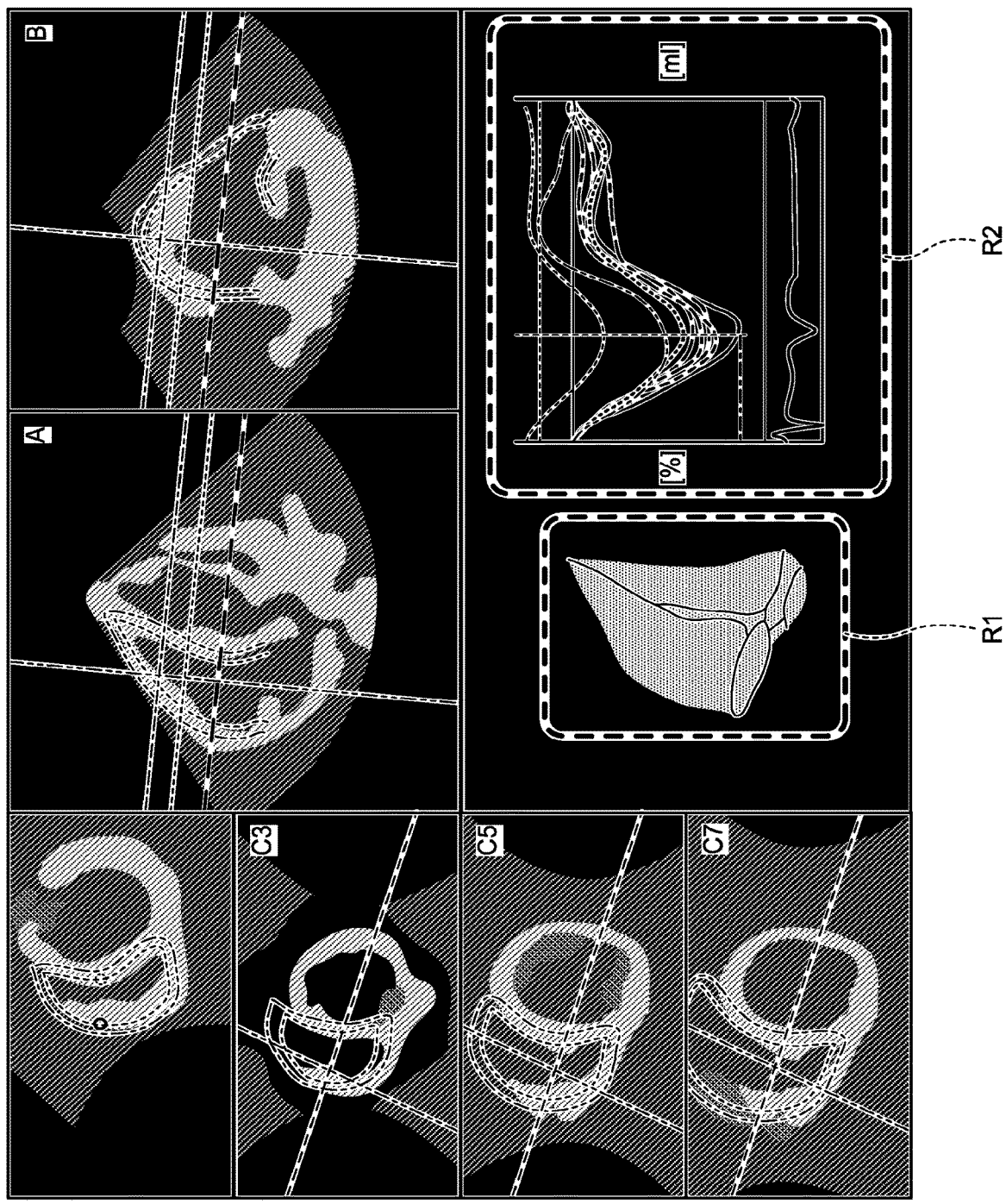
FIG. 6 is a diagram for description of the processing performed by the output control function according to the first embodiment.

FIGS. 5 and 6 are diagrams for description of processing performed by the output control function 176 according to the first embodiment. FIG. 5 illustrates exemplary display of the second calculation information. FIG. 6 illustrates exemplary display of the first calculation information. For example, the output control function 176 simultaneously displays the second calculation information illustrated in FIG. 5 and the first calculation information illustrated in FIG. 6 on the display 103.

As illustrated in FIG. 5, the output control function 176 displays on the display 103, as temporal change curves for one cardiac cycle, parameters of the annulus cross-sectional area "iArea", the mean annulus diameter "iDia_mean", the annulus diameter "iDia_A" between (S) and (L) corresponding to Surface A, and the annulus diameter "iDia_B" between (I) and (C) corresponding to Surface B. In the example illustrated in FIG. 5, the annulus diameter "iDia_B" is larger than the annulus diameter "iDia_A" for one cardiac cycle. The annulus diameter "iDia_mean" has a magnitude between the annulus diameter "iDia_A" and the annulus diameter "iDia_B" for one cardiac cycle. The annulus cross-sectional area "iArea" illustrated in FIG. 5 exhibits change similar to a temporal change curve of the right ventricular cavity volume (refer to a graph in Region R2 in FIG. 6).

The description with reference to FIG. 5 is merely exemplary, and the embodiment is not limited thereto. For example, the case in which the second calculation information is displayed as a temporal change curve is described with reference to FIG. 5, but the embodiment is not limited thereto. For example, the output control function 176 may display the second calculation information as numerical information such as a value in a predetermined cardiac phase (for example, ED or ES), the maximum value in one cardiac cycle, and the minimum value in one cardiac cycle. Such numerical information may be displayed as text information indicating a numerical value or may be displayed as a plot on an optional graph (for example, a temporal change curve in FIG. 5).

For example, the case in which the annulus cross-sectional area, the mean annulus diameter, and the annulus diameter at a predetermined position are displayed is described with reference to FIG. 5, but the annulus perimeter may be displayed. Specifically, the output control function 176 may optionally select and displays the second calculation information calculated by the second calculation function 175.

As illustrated in FIG. 6, the output control function 176 displays, on the display 103, sectional images of Surface A, Surface B, and four Surfaces C as MPR sectional images of reference sections used in 3DWMT of the right cardiac ventricle. In each sectional image, a position corresponding to the outline (inner outline and outer outline) of myocardium of the right cardiac ventricle is delineated with dashed lines together with a line marker indicating each section acquisition position. Each sectional image is preferably displayed as a moving image but may be displayed as a still image (for example, a still image of a cardiac phase specified by the operator).

As illustrated in Region R1 of FIG. 6, the output control function 176 converts the wall motion information (or volume information) calculated by the first calculation function 173 into a color code, and maps the color code on a rendering image. The rendering image is preferably an image generated by surface rendering processing on the inner outline of the right cardiac ventricle, but the embodiment is not limited thereto, and optional rendering processing on another site (such as the outer outline of the right cardiac ventricle) is applicable. The technology disclosed in Patent Literature 1 is applicable for a display image in Region R1. Specifically, by using the technology disclosed in Patent Literature 1, the output control function 176 can display the tubal inflow part (Inlet) including the tricuspid annulus and the tubal outflow part (RVOT) including the pulmonary artery annulus in addition to the inner outline of the right cardiac ventricle. The annular boundary position (ROI1 in FIG. 3) between the inner outline of the right cardiac ventricle and the tubal inflow part, and the annular boundary position (ROI2 in FIG. 3) between the inner outline of the right cardiac ventricle and the tubal outflow part can be changed (adjusted) by the operator while checking the rendering image. The rendering image on which the wall motion information is mapped is preferably displayed as a moving image but may be displayed as a still image (for example, a still image of a cardiac phase specified by the operator).

As illustrated in Region R2 of FIG. 6, the output control function 176 displays, as temporal change curves, the wall motion information (or volume information) calculated by the first calculation function 173. In the example illustrated in FIG. 6, the output control function 176 displays seven temporal change curves obtained by averaging the values of local wall motion information in predetermined seven segments (small regions) of the region of the right cardiac ventricle, a temporal change curve of the area change ratio (AC), and a temporal change curve of the volume of the right cardiac ventricle. Accordingly, the operator can evaluate the magnitude of a peak value of each wall motion information and evaluate a timing at which the peak value is detected. The output control function 176 may display the average of local temporal change curves of all segments as a global myocardial function index. Representative examples of the comprehensive myocardial function index include global longitudinal strain (GLS), global circumferential strain (GCS), and global area change ratio (GAC).

The description with reference to FIG. 6 is merely exemplary, and the embodiment is not limited thereto. For example, although not illustrated in FIG. 6, the output control function 176 may display the first calculation information (wall motion information, volume information) as a list (table) of numerical values. For example, the output control function 176 displays the volume information of the right cardiac ventricle as a list of EDV, ESV, EF, and the like. The output control function 176 is not limited to the form illustrated in FIG. 6 but may display the first calculation information by using the technology disclosed in Patent Literature 1 or any other well-known technology.

In this manner, the output control function 176 simultaneously displays the first calculation information and the second calculation information on the display 103. The above description is made with the case in which the first calculation information and the second calculation information are simultaneously output, but the embodiment is not limited thereto. For example, the output control function 176 may output the first calculation information and the second calculation information separately from each other. In this case, the output control function 176 preferably performs display of the first calculation information and display of the second calculation information in a switching manner in accordance with a switching operation from the operator.

For example, the output control function 176 may not only simultaneously output the first calculation information (cardiac ventricle information) and the second calculation information (annulus information) but also output information obtained by combining the first calculation information and the second calculation information. For example, the output control function 176 outputs, as the output information, a temporal change curve obtained by combining the first calculation information and the second calculation information. The temporal change curve is, for example, a graph in which the first calculation information and the second calculation information are indicated in temporal sequences identical to each other.

The output destination to which the output control function 176 outputs information is not limited to the display 103. For example, the output control function 176 may transmit information to an optional device connected through a network. Specifically, the output control function 176 may transmit information to a server device integrally managing data in a hospital or a device (report production device, for example) for producing a diagnosis report. For example, the output control function 176 may store information in a record media such as a digital versatile disc (DVD).

Figure 7:
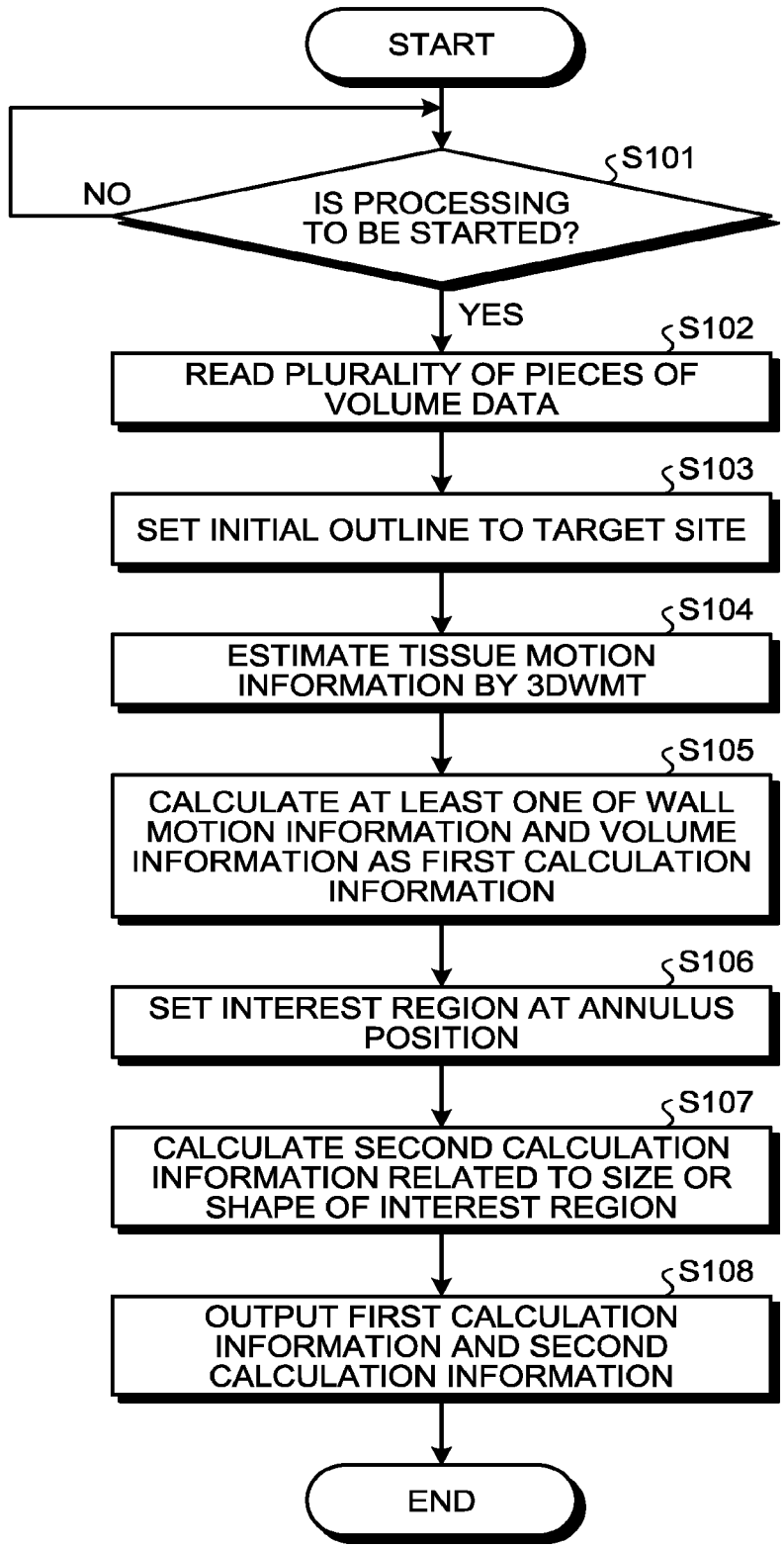
FIG. 7 is a flowchart illustrating the procedure of processing performed by the ultrasonic wave diagnostic apparatus according to the first embodiment.

FIG. 7 is a flowchart illustrating the procedure of processing performed by the ultrasonic wave diagnostic apparatus 100 according to the first embodiment. The processing procedure illustrated in FIG. 7 is started, for example, when an instruction to start analysis of the annulus part is received from the operator.

At step S101, it is determined whether processing is to be started. For example, the input interface 102 receives an instruction to start analysis of the annulus part from the operator, and transfers the received instruction to the processing circuitry 170. When having received the instruction forwarded by the input interface 102, the processing circuitry 170 determines that processing is to be started (positive determination at step S101), and starts processing at step S102 and later. When processing is not to be started (negative determination at step S101), the processing at step S102 and later is not started, and each processing function of the processing circuitry 170 remains in a waiting state.

Upon the positive determination step S101, the acquisition function 171 reads a plurality of pieces of volume data at step S102. For example, the acquisition function 171 reads, from the image memory 140, a plurality of pieces of volume data obtained through image capturing of the region including the right cardiac ventricle of the subject P for at least one cardiac cycle.

At step S103, the estimation function 172 sets an initial outline to a target site. For example, the estimation function 172 sets a three-dimensional initial outline to right cardiac ventricle included in volume data in a cardiac phase specified by operator. A plurality of tracking points are set to the initial outline.

At step S104, the estimation function 172 estimates tissue motion information by 3DWMT. For example, the estimation function 172 tracks the positions of the tracking points in the pieces of volume data performing track processing including pattern matching by using the volume data in which the tracking points are set in the initial phase and the volume data in the next phase.

At step S105, the first calculation function 173 calculates the first calculation information. For example, the first calculation function 173 calculates, as the first calculation information, information such as entire or local strain, the area change ratio, and the volume related to the right cardiac ventricle based on a result of the estimation by the estimation function 172.

At step S106, the setting function 174 sets a region of interest at the annulus position. For example, the setting function 174 sets the region of interest at a position corresponding to at least one of the tricuspid annulus and the pulmonary artery annulus as the annulus position.

At step S107, the second calculation function 175 calculates the second calculation information for the region of interest. For example, the second calculation function 175 calculates, for each cardiac phase based on the motion information related to a plurality of tracking points included in the region of interest among the tracking points, at least one parameter among the annulus diameter at a predetermined position, the annulus perimeter, the cross-sectional area of the annulus part, and the mean annulus diameter.

At step S108, the output control function 176 outputs the first calculation information and the second calculation information. For example, the output control function 176 outputs the second calculation information as at least one piece of information among a temporal change curve, a value in a predetermined cardiac phase, the maximum value in one cardiac cycle, and the minimum value in one cardiac cycle.

The processing procedure described with reference to FIG. 7 is merely exemplary, and the embodiment is not limited thereto. For example, the above-described processing procedure may be changed to an optional order without causing inconsistency to the contents of processing. For example, the processing at step S106 may be executed right after the processing at step S103 (before the processing at step S104).

As described above, the ultrasonic wave diagnostic apparatus 100 can present, to the operator, the dynamic change of the size of the annulus part and the magnitude thereof together with the entire or local wall motion information and volume information. Accordingly, the operator can quantitatively understand the degree of remodeling of the cardiac ventricle and the cardiac function, and simultaneously understand the dynamic change of the size of the annulus part and the magnitude thereof. As a result, the operator can effectively select a method of medical treatment of disorder of the annulus part and a medical treatment device.

For example, as compensation for decrease of the cardiac function, the heart expands, and the annulus part expands (for example, the annulus diameter increases) along with the expansion, and as a result, blockage incompetence (backflow) of a valve occurs in some cases. In such a case, for example, a medical treatment method is applied in which a string-shaped medical instrument (annulus ligation device) is embedded around the valve and narrowed down to reduce the increased annulus diameter. The ultrasonic wave diagnostic apparatus 100 according to the present embodiment can provide information such as the annulus diameter and the annulus perimeter to support selection of an annulus ligation device of an optimum size and kind. In addition, the ultrasonic wave diagnostic apparatus 100 can provide quantitative cardiac function information such as the wall motion information to support determination of an appropriate medical treatment timing.

The first embodiment describes above the case in which the ultrasonic wave diagnostic apparatus 100 according to the present embodiment is applied to analysis of the right cardiac ventricle, but the embodiment is not limited thereto. For example, the ultrasonic wave diagnostic apparatus 100 is also applicable to analysis of the left cardiac ventricle in a manner similar to that for the right cardiac ventricle.

The first embodiment describes above the case in which analysis is performed for a duration including at least one cardiac cycle, but the embodiment is not limited thereto. For example, the embodiment is applicable to a case in which analysis may be performed for an optional duration shorter than one cardiac cycle. Specifically, the acquisition unit acquires a plurality of pieces of volume data obtained through image capturing of a region including the cardiac ventricle of a subject for a predetermined duration. The predetermined duration corresponds to, for example, a duration including at least one cardiac cycle.

Second Embodiment

The first embodiment describes above the case in which the second calculation information related to the size of the region of interest is calculated, but the embodiment is not limited thereto. For example, the ultrasonic wave diagnostic apparatus 100 may calculate the second calculation information related to the shape of the region of interest.

For example, the tricuspid annulus is known to have a stereoscopic structure of an inverted horseshoe shape (also called saddle shape) that is high in the direction from the anterior cusp to the posterior cusp and low in the direction from the septum to the sidewall. However, in a case of tricuspid valve close incompetence, particularly in a severe case of bad prognosis, the saddle shape is known to be flattened as compared to a normal case. Thus, in a second embodiment, the ultrasonic wave diagnostic apparatus 100 calculates a height difference attributable to the shape as the second calculation information related to the shape of the region of interest.

The ultrasonic wave diagnostic apparatus 100 according to the second embodiment has a configuration same as that of the ultrasonic wave diagnostic apparatus 100 exemplarily illustrated in FIG. 1, and has a difference in part of processing performed by the second calculation function 175. Thus, the second embodiment mainly describes the difference from the first embodiment, and omits description of any component having a function same as that described in the first embodiment.

The second calculation function 175 according to the second embodiment calculates the second calculation information related to the shape of the region of interest based on a result of the estimation by the estimation function 172. The second calculation function 175 calculates a local height difference of the annulus part as the second calculation information related to the shape of the region of interest. Specifically, the second calculation function 175 calculates the local height difference of the annulus part based on the positions (coordinate information) of a plurality of tracking points included in the region of interest among a plurality of tracking points. The local height difference of the annulus part is exemplary "annulus shape information".

Figure 8:
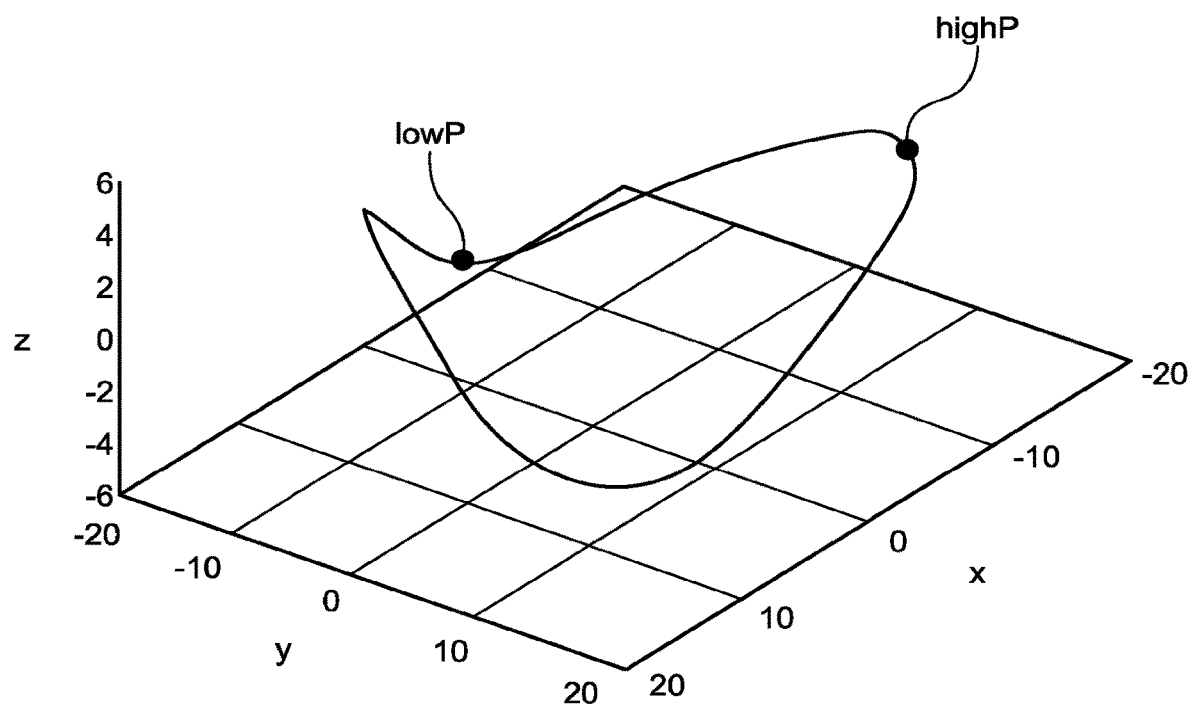
FIG. 8 is a diagram for description of processing performed by a second calculation function according to a second embodiment.

FIG. 8 is a diagram for description of the processing performed by the second calculation function 175 according to the second embodiment. FIG. 8 exemplarily illustrates the three-dimensional shape of ROI1 corresponding to the tricuspid annulus. The three-dimensional shape of ROI1 is delineated by connecting the positions (coordinate information) of a plurality of tracking points included in ROI1. In the second embodiment, the setting function 174 preferably sets the region of interest in the saddle shape by using two sectional images of Surface A and Surface B and interpolation processing.

As illustrated in FIG. 8, the second calculation function 175 calculates the barycenter position of the tracking points included in ROI1. Then, the second calculation function 175 calculates a regression plane passing through the calculated barycenter position, and calculates the local height difference of the annulus part by using the direction (axis) of the normal vector of the regression plane. Specifically, the second calculation function 175 calculates the distance (height) of each point on the annulus part (ROI1) from the regression plane in the direction of the normal vector. Then, the second calculation function 175 specifies, as a highest point "highP", a point highest relative to the regression plane (closest to the atrium side). In addition, the second calculation function 175 specifies, as a lowest point "lowP", a point lowest relative to the regression plane (closest to the heart apex). When the highest point "highP" has a positive value, the lowest point "lowP" has a negative value. Then, the second calculation function 175 calculates, as the local height difference "ΔH" of the annulus part, the difference between the highest point highP and the lowest point lowP in the direction of the normal vector. Accordingly, the local height difference "ΔH" of the annulus part corresponds to the sum of the distance (absolute value) from the regression plane to the highest point highP and the distance (absolute value) from the regression plane to the lowest point lowP.

The local height difference "ΔH" of the annulus part can be defined in each cardiac phase "t", and thus can be calculated as a function indicating temporal change. Specifically, the second calculation function 175 defines a highest point "highP(t)" and a lowest point "lowP(t)" as described above in the initial phase "t=0" in 3DWMT. Then, the second calculation function 175 calculates the difference between the highest point "highP(t)" and the lowest point "lowP(t)" as the local height difference "ΔH(t)" of the annulus part in each cardiac phase (t).

In this manner, the second calculation function 175 calculates the local height difference "ΔH(t)" of the annulus part for ROI1 corresponding to the tricuspid annulus. The above description is made with the case in which annulus shape information of the tricuspid annulus is calculated, but the embodiment is not limited thereto. For example, the second calculation function 175 may calculate the same annulus shape information for an annulus part such as the pulmonary artery annulus or the left cardiac ventricle.

Then, the output control function 176 outputs the calculated local height difference "ΔH(t)" of the annulus part. The output form and output destination of the local height difference "ΔH(t)" of the annulus part are same as those described in the first embodiment. Specifically, the output control function 176 preferably displays the local height difference "ΔH(t)" of the annulus part as a temporal change curve, but may display numerical information such as a value in a predetermined cardiac phase (for example, ED or ES), the maximum value in one cardiac cycle, and the minimum value in one cardiac cycle. Such numerical information may be displayed as text information indicating a numerical value or may be displayed as a plot on an optional graph (for example, a temporal change curve in FIG. 5).

In addition, the output control function 176 may display the three-dimensional shape of the annulus part (tricuspid annulus) on the display 103 as illustrated in FIG. 8.

In this manner, the ultrasonic wave diagnostic apparatus 100 according to the second embodiment can calculate temporally sequential annulus shape information and present the calculated temporally sequential annulus shape information to the operator. Accordingly, the operator can easily determine whether the saddle shape is flattened and can understand temporal change thereof, and thus can easily perform detailed evaluation of the clinical condition of the annulus part.

Other Embodiments

The embodiment may be performed in various kinds of different forms other than the above-described embodiments.

Medical Information Processing Apparatus

The above-described embodiments describe the examples in which the disclosed technology is applied to the ultrasonic wave diagnostic apparatus 100, but the embodiment is not limited thereto. For example, the disclosed technology may be applied to a medical information processing apparatus 200. The medical information processing apparatus 200 corresponds to, for example, a work station, a picture archiving communication system (PACS) viewer, or a console device of another medical image diagnostic apparatus. The other medical image diagnostic apparatus corresponds to, for example, a magnetic resonance imaging (MRI) device or an X-ray computed tomography (CT) device. When the MRI device or the X-ray CT device is used as the medical information processing apparatus, the medical information processing apparatus may execute the disclosed technology by using volume data (MR image data, CT image data) captured by each medical image diagnostic apparatus.

Figure 9:
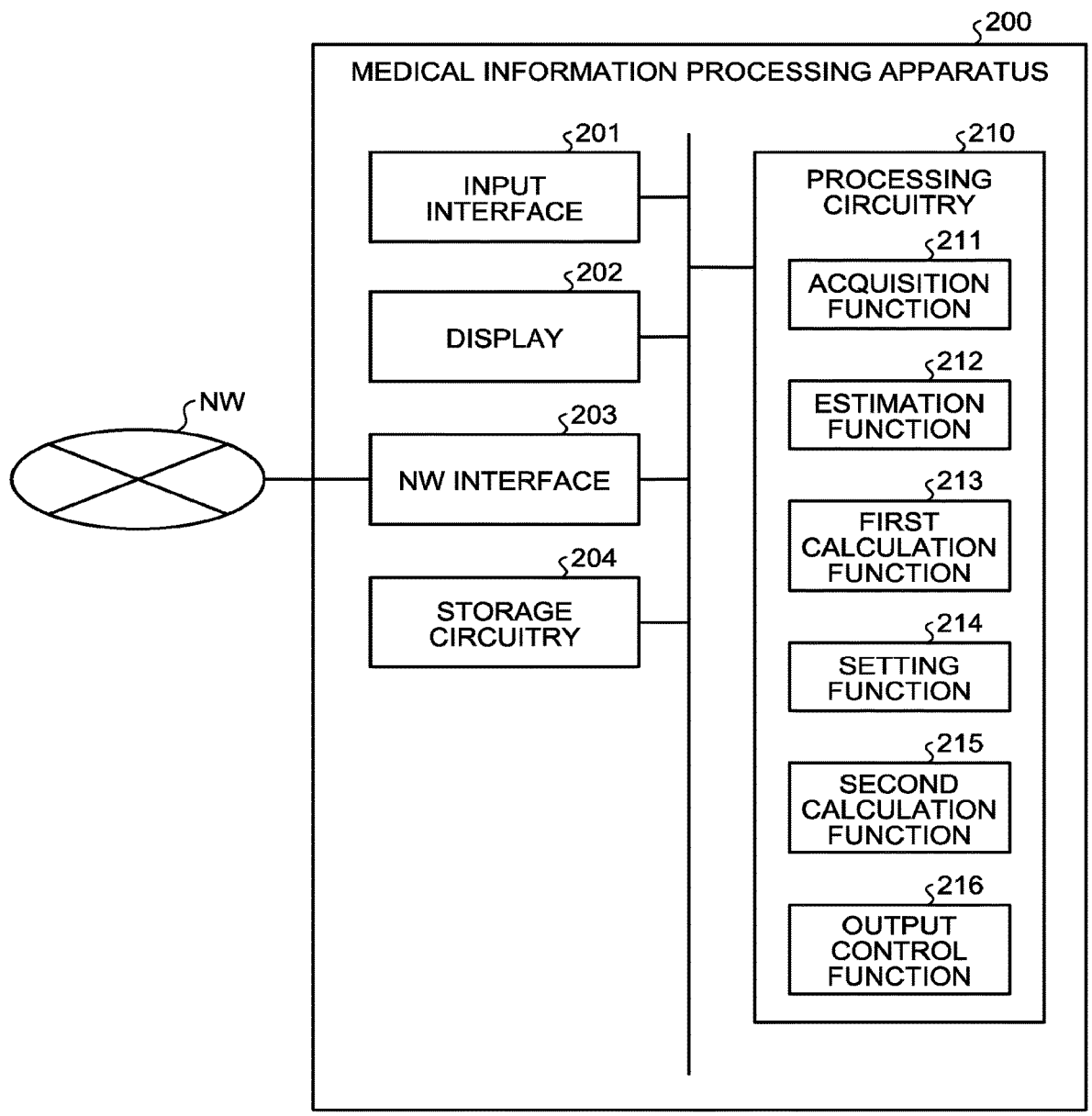
FIG. 9 is a block diagram illustrating an exemplary configuration of a medical information processing apparatus according to another embodiment.

FIG. 9 is a block diagram illustrating an exemplary configuration of the medical information processing apparatus 200 according to another embodiment. As illustrated in FIG. 9, the medical information processing apparatus 200 includes an input interface 201, a display 202, a NW interface 203, a storage circuitry 204, and a processing circuitry 210. The input interface 201, the display 202, the NW interface 203, and the processing circuitry 210 are connected with each other to perform communication therebetween.

The input interface 201 is an input device such as a mouse, a keyboard, or a touch panel for receiving various instructions and setting requests from the operator. The display 202 is a display device configured to display a medical image and display a GUI through which the operator inputs various setting requests by using the input interface 201.

The NW interface 203 controls communication performed between the medical information processing apparatus 200 and an external device. Specifically, the NW interface 203 receives various kinds of information from the external device, and outputs the received information to the processing circuitry 210. The NW interface 203 is achieved by, for example, a network card, a network adapter, or a network interface controller (NIC).

The storage circuitry 204 is, for example, a NAND (Not AND) flash memory or a hard disk drive (HDD) and stores various computer programs for displaying medical image data and a GUI, and information to be used by the computer programs.

The processing circuitry 210 is an electronic device (processor) configured to control the entire processing at the medical information processing apparatus 200. The processing circuitry 210 executes an acquisition function 211, an estimation function 212, a first calculation function 213, a setting function 214, a second calculation function 215, and an output control function 216. The acquisition function 211, the estimation function 212, the first calculation function 213, the setting function 214, the second calculation function 215, and the output control function 216 are recorded, for example, in the form of computer-executable computer program in the storage circuitry 204. The processing circuitry 210 reads and executes each computer program to achieve a function (the acquisition function 211, the estimation function 212, the first calculation function 213, the setting function 214, the second calculation function 215, or the output control function 216) corresponding to the read computer program.

For example, the acquisition function 211 acquires a plurality of pieces of volume data (such as ultrasonic wave image data, MR image data, or CT image data) obtained through image capturing of a region including the cardiac ventricle of the subject P for at least one cardiac cycle. The estimation function 212 estimates motion of tissue of the cardiac ventricle by using the pieces of volume data. The first calculation function 213 calculates the first calculation information including at least one of the wall motion information and the volume information related to the cardiac ventricle based on a result of the estimation by the estimation function 172. The setting function 214 sets a region of interest corresponding to the annulus position of a valve related to inflow or outflow of blood current at the cardiac ventricle. The second calculation function 215 calculates the second calculation information related to the size or shape of the region of interest based on a result of the estimation by the estimation function 172. The output control function 216 outputs the first calculation information and the second calculation information. Accordingly, the medical information processing apparatus 200 can appropriately analyze the size or shape of the annulus part.

The term "processor" used in the above description means, for example, a central processing unit (CPU), a graphics processing unit (GPU), or a circuit such as an application specific integrated circuit (ASIC), a programmable logic device (for example, a simple programmable logic device (SPLD), a complex programmable logic device (CPLD), or a field programmable gate array (FPGA)). The processor achieves a function by reading and executing a computer program stored in the storage circuitry 150. The computer program may be directly incorporated in a circuit of the processor instead of being stored in the storage circuitry 150. In this case, the processor achieves the function by reading and executing the computer program incorporated in the circuit. The processors in the present embodiment are not limited to a configuration in which each processor is configured as a single circuit, but a plurality of independent circuits may be combined as one processor to achieve the function. Moreover, a plurality of components in the drawings may be integrated on one processor to achieve the function.

Each component of each device described above is functionally conceptual and does not necessarily need to be physically configured as illustrated in the drawings. In other words, the specific form of distribution and integration of the devices is not limited to those illustrated in drawings, but the entire or part thereof may be functionally or physically distributed and integrated in arbitrary units in accordance with, for example, various loads and use statuses. Moreover, the entire or an optional part of each processing function performed at each device may be achieved by a CPU and a computer program analyzed and executed by the CPU or may be achieved as wired logic hardware.

Among the pieces of processing described in the above-described embodiments, the entire or part of processing described as automatically performed processing may be manually performed, or the entire or part of processing described as manually performed processing may be automatically performed by a well-known method. In addition, information described in the above-described document and drawings and including processing procedures, control procedures, specific names, various kinds of data and parameters may be optionally changed unless otherwise stated.

The medical information processing method in the above-described embodiments can be achieved by executing a medical information processing program prepared in advance through a computer such as a personal computer or a work station. The medical information processing program may be distributed through a network such as the Internet. In addition, the medical information processing program may be recorded in a computer-readable recording medium such as a hard disk, a flexible disk (FD), a CD-ROM, an MO, or a DVD, read from the recording medium by a computer, and executed.

According to at least one embodiment described above, it is possible to appropriately analyze the size and shape of an annulus part.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
    processing circuitry configured to
        acquire a plurality of pieces of volume data obtained through image capturing of a region including a right cardiac ventricle of a subject for a predetermined duration;
        set a plurality of first tracking points corresponding to an outline of the right cardiac ventricle in the plurality of pieces of volume data;
        receive, from a user, four designated points including an annulus position on a septum side, an annulus position on a sidewall side, an annulus position on a lower wall side, and an annulus position on a supraventricular crest side, among the set plurality of first tracking points;
        set a plurality of second tracking points, each corresponding to a position on an annulus having a saddle shape, by interpolating the received designated points through interpolation processing performed along the saddle shape;
        estimate motion of tissue of the right cardiac ventricle by tracking positions of the plurality of second tracking points in the plurality of pieces of volume data;
        calculate, based on the estimated motion, cardiac ventricle information indicating at least one of wall motion information and volume information related to the right cardiac ventricle;
        calculate, based on the positions of the plurality of second tracking points, annulus information indicating a size or shape of an annulus position of a valve related to inflow or outflow of blood current at the right cardiac ventricle; and
        output the cardiac ventricle information and the annulus information.

2. The medical information processing apparatus according to claim 1, wherein the processing circuitry is further configured to set, as the annulus position of the valve, a position corresponding to at least one of a tricuspid annulus and a pulmonary artery annulus.

3. The medical information processing apparatus according to claim 1, wherein the processing circuitry is further configured to
    display the annulus position of the valve, and
    receive an input operation to change the displayed annulus position from an operator and change the annulus position in accordance with the received input operation.

4. The medical information processing apparatus according to claim 3, wherein the processing circuitry is further configured to display the annulus position of the valve on a rendering image generated from the volume data.

5. The medical information processing apparatus according to claim 1, wherein the processing circuitry is further configured to calculate, as the annulus information for each cardiac phase, at least one parameter among an annulus perimeter, an annulus diameter at a predetermined position, a cross-sectional area of an annulus part, a mean annulus diameter, and a local height difference of the annulus part.

6. The medical information processing apparatus according to claim 5, wherein the processing circuitry is further configured to calculate an annulus diameter at the annulus position on a multi planer reconstruction (MPR) sectional image specified by an operator.

7. The medical information processing apparatus according to claim 5, wherein the processing circuitry is further configured to calculate the cross-sectional area of the annulus part as a curved surface by using a barycenter position of the plurality of second tracking points and a position of each of the second tracking points.

8. The medical information processing apparatus according to claim 7, wherein the processing circuitry is further configured to calculate the mean annulus diameter based on an assumption that the cross-sectional area of the annulus part is equal to the area of a circle.

9. The medical information processing apparatus according to claim 1, wherein the predetermined duration corresponds to a duration including at least one cardiac cycle.

10. The medical information processing apparatus according to claim 9, wherein the processing circuitry is further configured to output the annulus information as at least one piece of information among a temporal change curve, a value in a predetermined cardiac phase, a maximum value in the one cardiac cycle, and a minimum value in the one cardiac cycle.

11. The medical information processing apparatus according to claim 1, wherein the processing circuitry is further configured to calculate, as the wall motion information, at least one of displacement in a predetermined direction, strain in a predetermined direction, and an area change ratio that are entirely or locally defined for the right cardiac ventricle.

12. The medical information processing apparatus according to claim 1, wherein the processing circuitry is further configured to calculate the annulus information for each of a plurality of phases included in the predetermined duration.

13. The medical information processing apparatus according to claim 1, wherein the processing circuitry is further configured to calculate the annulus information based on the estimated motion at the plurality of second tracking points.

14. The medical information processing apparatus according to claim 1, wherein the processing circuitry is further configured to output information obtained by combining the cardiac ventricle information and the annulus information.

15. The medical information processing apparatus according to claim 14, wherein the processing circuitry is further configured to output, as the output information, a temporal change curve obtained by combining the cardiac ventricle information and the annulus information.

16. The medical information processing apparatus according to claim 1, wherein the medical information processing apparatus is an ultrasonic wave diagnostic apparatus.

17. A non-transitory computer-readable recording medium including a plurality of instructions executable by a computer, wherein the instructions, when executed by the computer, cause the computer to execute a method comprising:

acquiring a plurality of pieces of volume data obtained through image capturing of a region including a right cardiac ventricle of a subject for a predetermined duration;

setting a plurality of first tracking points corresponding to an outline of the right cardiac ventricle in the plurality of pieces of volume data;

receiving, from a user, four designated points including an annulus position on a septum side, an annulus position on a sidewall side, an annulus position on a lower wall side, and an annulus position on a supraventricular crest side, among the set plurality of first tracking points;

setting a plurality of second tracking points, each corresponding to a position on an annulus having a saddle shape, by interpolating the received designated points through interpolation processing performed along the saddle shape;

estimating motion of tissue of the right cardiac ventricle by tracking positions of the plurality of second tracking points in the plurality of pieces of volume data;

calculating, based on the estimated motion, cardiac ventricle information indicating at least one of wall motion information and volume information related to the right cardiac ventricle;

calculating, based on the positions of the plurality of second tracking points, annulus information indicating a size or shape of an annulus position of a valve related to inflow or outflow of blood current at the right cardiac ventricle; and outputting the cardiac ventricle information and the annulus information.

* * * * *